(12) United States Patent
Meetz et al.

(10) Patent No.: US 8,216,200 B2
(45) Date of Patent: Jul. 10, 2012

(54) DISPOSABLE ABSORBENT ARTICLE WITH DISPOSAL TAB

(75) Inventors: Nancy Darlene Meetz, Appleton, WI (US); Michael Donald Sperl, Waupaca, WI (US); Michael John Faulks, Neenah, WI (US); Robert Lee Popp, Hortonville, WI (US); Sandra Marie Rogers, Appleton, WI (US); Troy Leonard Tipton, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 366 days.

(21) Appl. No.: 12/575,107

(22) Filed: Oct. 7, 2009

(65) Prior Publication Data

US 2011/0082436 A1    Apr. 7, 2011

(51) Int. Cl.
*A61F 13/15*    (2006.01)
(52) U.S. Cl. .............. 604/385.13; 604/387; 604/389; 604/391; 604/394; 604/396; 604/386
(58) Field of Classification Search ............. 604/385.13, 604/385.01, 387, 389, 391, 394, 396, 386
See application file for complete search history.

(56) References Cited

U.S. PATENT DOCUMENTS

| | | | |
|---|---|---|---|
| 5,133,707 A | 7/1992 | Rogers et al. | |
| 5,531,731 A | 7/1996 | Brusky | |
| 5,531,732 A | 7/1996 | Wood | |
| 5,560,798 A | 10/1996 | Brusky | |
| 5,624,429 A | 4/1997 | Long et al. | |
| 5,759,181 A | 6/1998 | Sayama et al. | |
| 6,213,991 B1 | 4/2001 | Kling et al. | |
| 6,302,871 B1 | 10/2001 | Nakao et al. | |
| 6,454,751 B1* | 9/2002 | Olson | 604/389 |
| D483,867 S | 12/2003 | Klebba et al. | |
| 6,730,069 B2 | 5/2004 | Tanzer et al. | |
| 7,373,698 B2 | 5/2008 | Erdman et al. | |
| 7,425,242 B2 | 9/2008 | Olsson et al. | |
| 2002/0032427 A1 | 3/2002 | Schmitz et al. | |
| 2004/0236301 A1 | 11/2004 | Wendelstorf et al. | |
| 2005/0101930 A1 | 5/2005 | Tachauer et al. | |
| 2007/0036939 A1 | 2/2007 | Ferry et al. | |
| 2007/0073261 A1 | 3/2007 | Ashton et al. | |
| 2007/0130732 A1 | 6/2007 | Matsumura et al. | |
| 2007/0250029 A1 | 10/2007 | Popp et al. | |
| 2008/0097363 A1 | 4/2008 | Fernfors et al. | |
| 2008/0132865 A1 | 6/2008 | Li et al. | |
| 2008/0154227 A1 | 6/2008 | Andersson et al. | |
| 2009/0068393 A1 | 3/2009 | Homolle et al. | |

FOREIGN PATENT DOCUMENTS

WO    WO 2008/142634 A2    11/2008

\* cited by examiner

*Primary Examiner* — Jacqueline F. Stephens
(74) *Attorney, Agent, or Firm* — Randall W. Fieldhack (57) ABSTRACT

An absorbent article is provided for personal wear about a wearer's waist. The article includes a pair of front side panels attached to the front waist region and a pair of back side panels attached to the back waist region, and is configurable from a wear configuration to a disposal configuration in which the article is generally compacted for disposal. The article also includes a disposal tab having an attachment region with an attachment width and a tab region with a gripping width, the attachment region attached to one of the front or back side panels, the tab region being attachable to the article in at least the disposal configuration of the article, wherein the attachment width is substantially equal to the gripping width.

17 Claims, 6 Drawing Sheets

DISPOSABLE ABSORBENT ARTICLE WITH DISPOSAL TAB

BACKGROUND

The present invention relates generally to absorbent articles intended for personal wear, and more particularly to disposable absorbent articles.

Many absorbent articles intended for personal wear, e.g., such as diapers, training pants, feminine hygiene products, adult incontinence products, bandages, medical garments and the like are designed to be sufficiently absorbent to pull moisture from liquid body exudates including urine, menses, blood, etc. away from the wearer to reduce skin irritation caused by prolonged wetness exposure. Diapers, as an example, are typically placed and secured on a wearer using a set of primary fastening tabs, such as adhesive tabs or mechanical (e.g., hook or loop) fastening system tabs and left in place to absorb insults as well as to contain fecal waste. When the diaper is to be disposed of, the caregiver will sometimes fold the diaper into a more compact configuration and secure the diaper in this configuration using the primary fastening tabs.

Training pants, unlike diapers, typically come pre-assembled in a wear configuration to more closely resemble conventional underpants. In particular, front and back waist regions of such training pants are typically attached either permanently or refastenably (such as by a primary fastening system) to define a wear configuration of the pants having a waist opening and leg openings.

For such articles where the attachment is refastenable, such as diapers and training pants, pop-opens (separation of the fasteners) can sometimes occur as a result of stresses placed on the attachment by movement of the wearer. For training pants, when a refastenable arrangement is used, the pants can be removed without unfastening, thereby also leaving no fasteners for use in holding the pants compact for disposal. Also, because the fastening components are not visible when the pants are worn there is no positive visual awareness provided to the consumer of such refastenability. Where a permanent attachment is used in such training pants, no fastening system is available for retaining the pants in a compact disposal configuration.

The fastening tabs provided on diapers are relatively small in the longitudinal direction of the diapers. Rather, they are typically much longer in the transverse direction because they are used for pulling the back of the diaper around the wearer and fastening to the front of the diaper. The sides of the diaper are relatively short in length (e.g., from waist opening to leg opening) so control of the sides of the diaper is simple using the small (in the longitudinal direction) fastening tabs provided on diapers. The sides of training pants, however, are typically much longer from the waist opening to the leg openings and therefore more difficult to manipulate with a tab as small as those used on diapers.

SUMMARY

There is a need, therefore, for a disposal fastening system provided on an absorbent article such as training pants for improved resistance to pop-opens, and for securing the article in a compact disposal configuration while providing a sufficient visual awareness to the consumer of the presence of such a fastening system and sufficient operability and use of such a fastening system.

In one aspect, an absorbent article is provided for personal wear about a wearer's waist. The article includes a liquid permeable inner surface for facing the wearer, an outer surface for facing away from the wearer, an absorbent body disposed therebetween, and a front waist region, a back waist region, and a crotch region extending longitudinally between and interconnecting the front and back waist regions. The article also includes a pair of front side panels attached to the front waist region and a pair of back side panels attached to the back waist region, the front and back side panels being one of permanently attached and releasably attachable to define a wear configuration of the absorbent article having a waist opening and a pair of leg openings spaced from the waist opening, wherein the front and back side panels each extend from the waist opening to one of the leg openings, the article being configurable from the wear configuration to a disposal configuration in which the article is generally compacted for disposal. Finally, the article also includes a disposal tab having an attachment region with an attachment width and a tab region with a gripping width, the attachment region attached to one of the front or back side panels, the tab region being attachable to the article in at least the disposal configuration of the article, wherein the attachment width is substantially equal to the gripping width.

In another aspect, an absorbent article for personal wear about a wearer's waist generally includes a liquid permeable inner surface for facing the wearer, an outer surface for facing away from the wearer, an absorbent body disposed therebetween, a front waist region, a back waist region, and a crotch region extending longitudinally between and interconnecting the front and back waist regions. The article also includes a pair of front side panels attached to the front waist region and a pair of back side panels attached to the back waist region, the front and back side panels being releasably attachable to define a wear configuration of the absorbent article having a waist opening and a pair of leg openings spaced from the waist opening, wherein the front and back side panels each extend from the waist opening to one of the leg openings, the article being configurable from the wear configuration to a disposal configuration in which the article is generally compacted for disposal. The article also includes an article fastening system for releasably attaching each front side panel to one of the back side panels, the article fastening system comprising an article mechanical fastener sufficient to maintain the article in a wear configuration during use of the article by the wearer, and a disposal tab having an attachment region with an attachment width and a tab region with a gripping width, the attachment width being substantially equal to the gripping width, the attachment region attached to one of the front or back side panels, the tab region having at least one substantially orthogonal corner distal from the attachment region and a grip region, the grip region being disposed transversely outward of the attachment region and generally non-attachable to the article at least in the wear configuration of the article for use in gripping the tab region of the disposal tab. Finally, the article also includes a disposal fastening system at least in part separate from the article fastening system for selectively releasably attaching the tab region of the disposal tab to the article in each of the wear configuration and the disposal configuration of the article, the disposal fastening system comprising a disposal mechanical fastener insufficient to maintain the article in a wear configuration during use of the article by the wearer.

Other features of the invention will be in part apparent and in part pointed out hereinafter. Other objects and advantages of the present disclosure will become more apparent to those skilled in the art in view of the following description and the accompanying drawings.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

It is to be understood by one of ordinary skill in the art that the present discussion is a description of exemplary aspects of the present disclosure only, and is not intended as limiting the broader aspects of the present disclosure.

Figure 1:
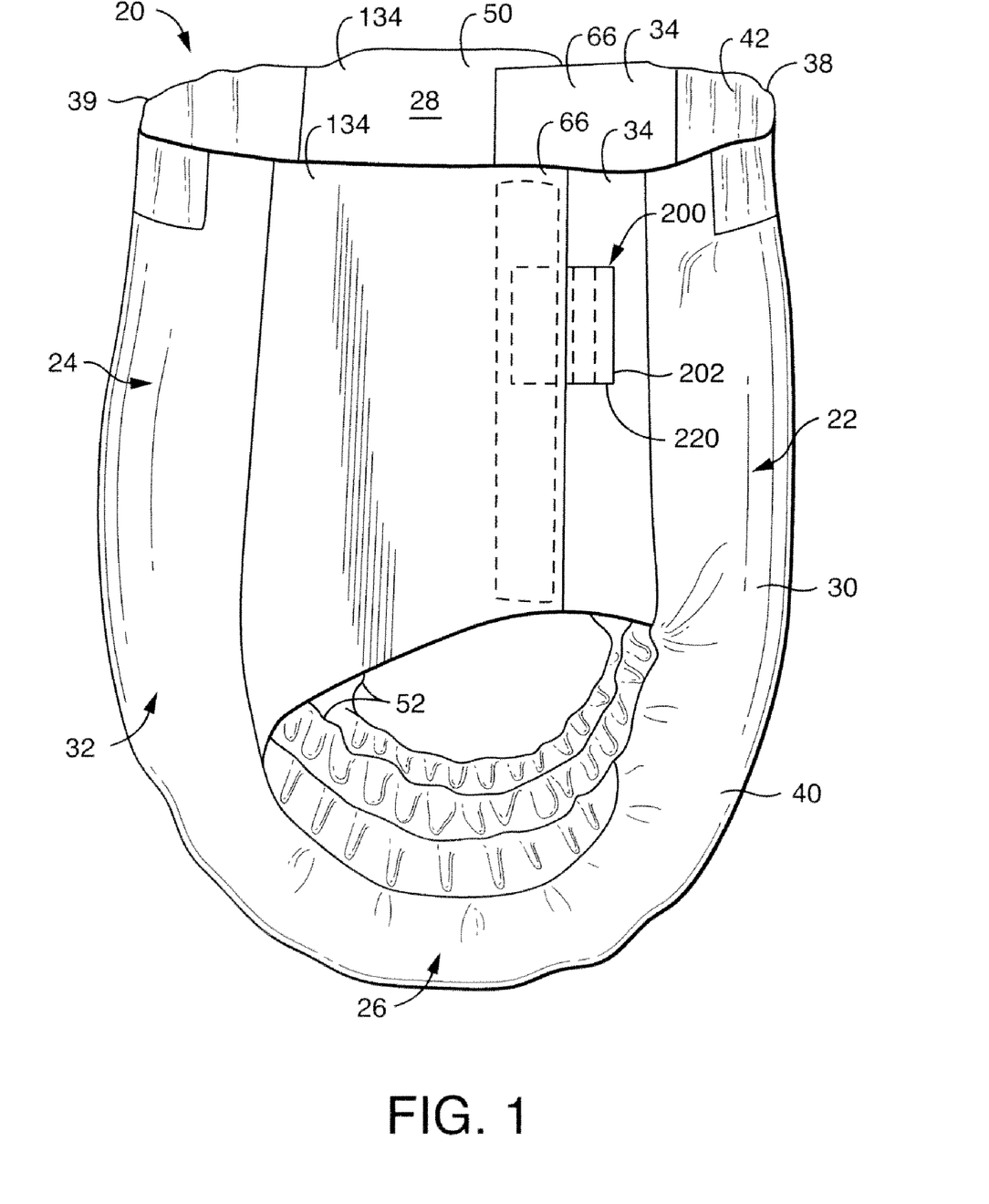
FIG. 1 is a side perspective of one aspect of a personal wear article in the form of a pair of training pants having a secondary or disposal fastening system illustrated in a fastened condition thereof.

Referring now to the drawings and in particular to FIG. 1, a personal wear absorbent article according to one aspect is illustrated in the form of a pants-type article for wear about a wearer's waist, and more particularly in the form of children's toilet training pants, indicated in its entirety by the reference numeral 20. The term absorbent generally refers to articles that can be placed against or in proximity to the body of the wearer to absorb and/or retain various liquid wastes discharged from the body. The absorbent article can be disposable, which refers to articles that are intended to be discarded after a limited period of use instead of being laundered or otherwise restored for reuse. It is understood that the concepts described herein are suitable for use with various other pants-type articles such as adult incontinence articles, as well as other articles intended for personal wear such as clothing, diapers, feminine hygiene products, medical garments, surgical pads and bandages, other personal care or health care garments, and the like without departing from the scope of the present invention.

By way of illustration only, various materials and methods for constructing the training pants 20 are disclosed in PCT Patent Application WO 00/37009 published Jun. 29, 2000 by A. Fletcher et al; U.S. Pat. No. 4,940,464 issued Jul. 10, 1990 to Van Gompel et al.; and U.S. Pat. No. 5,766,389 issued Jun. 16, 1998 to Brandon et al., which are incorporated herein by reference.

Figure 2:
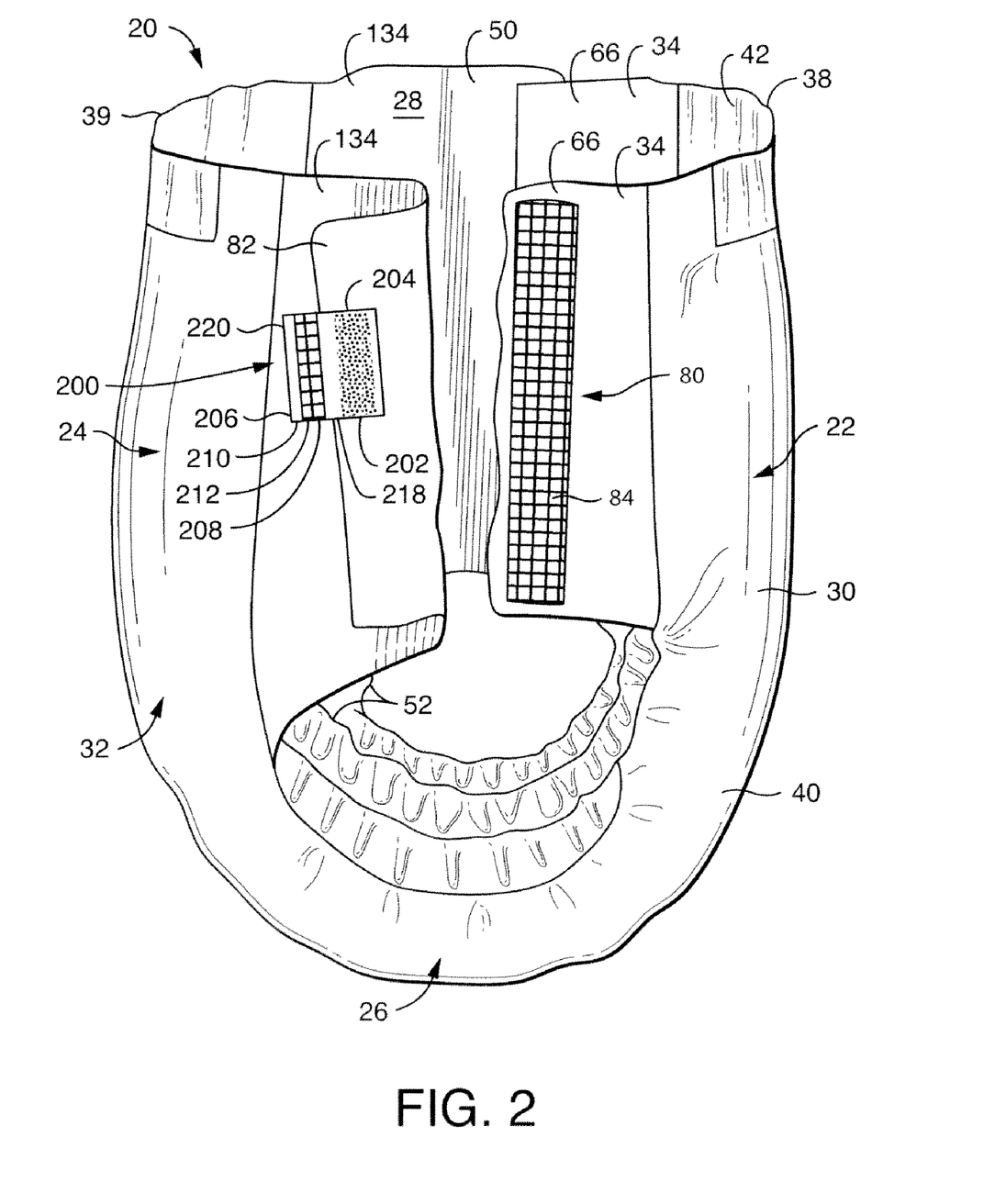
FIG. 2 is a side perspective similar to FIG. 1 with a primary, or article fastening system of the training pants in a unfastened condition on one side of the training pants and the disposal fastening system also in an unfastened condition.

The pair of training pants 20 is illustrated in FIG. 1 in a fully pre-assembled (i.e., as assembled during initial manufacture) configuration (broadly referred to herein as a wear configuration of the pants, i.e., absorbent article) and in FIG. 2 in a partially unfastened condition. The training pants 20 includes a front waist region 22, a back waist region 24, a crotch region 26 extending longitudinally between and interconnecting the front and back waist regions along a longitudinal direction of the pants, an inner surface 28 configured for contiguous relationship with the wearer, and an outer surface 30 opposite the inner surface. With additional reference to FIGS. 3 and 4, the training pants 20 also has a pair of laterally opposite side edges 36 and a pair of longitudinally opposite waist edges, respectively designated front waist edge 38 and back waist edge 39. The front waist region 22 is contiguous with the front waist edge 38, and the back waist region 24 is contiguous with the back waist edge 39.

Figure 3:
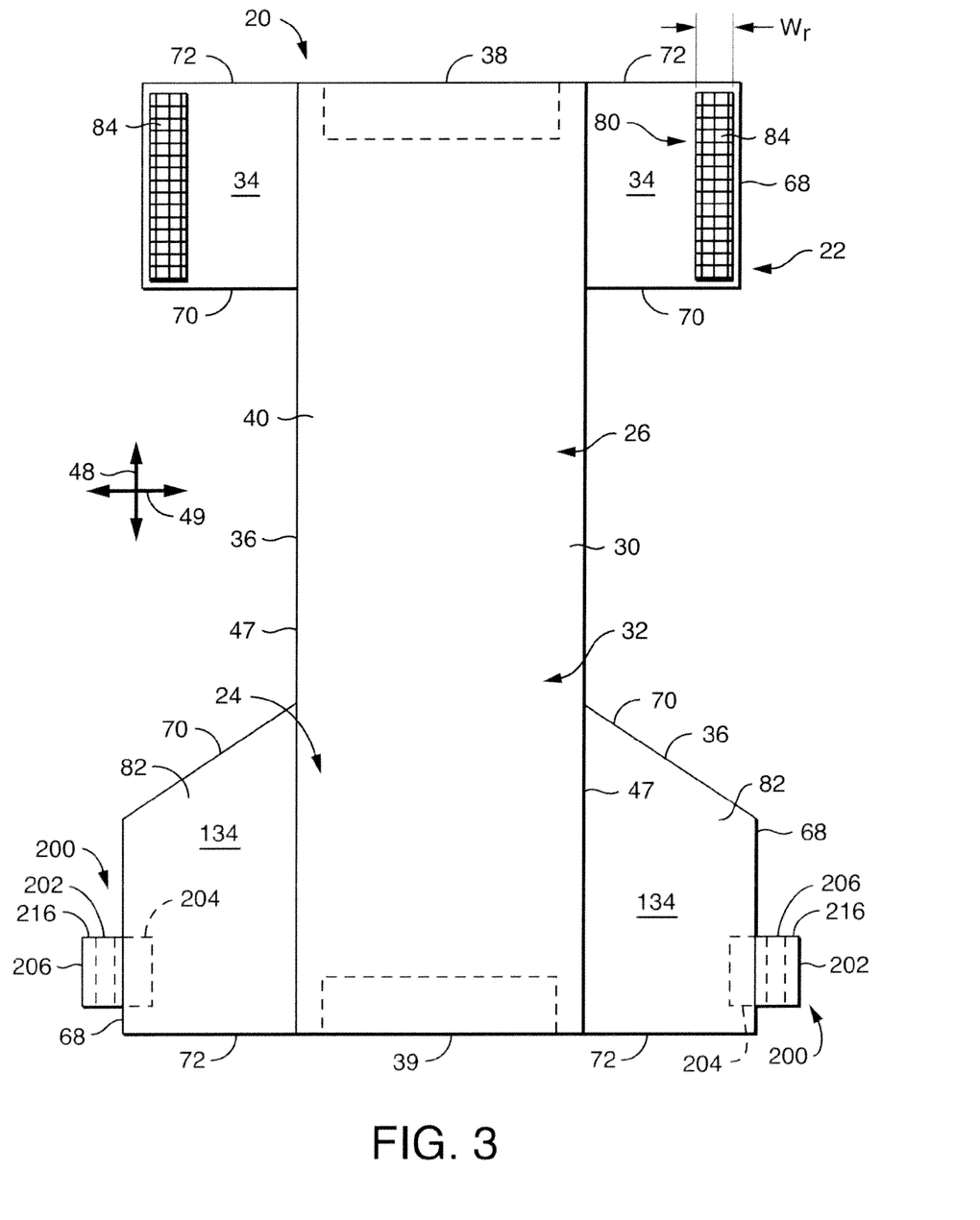
FIG. 3 is a bottom plan view of the training pants of FIG. 1 in an unfastened, unfolded and laid flat condition, and showing the surface of the training pants that faces away from the wearer.
Figure 4:
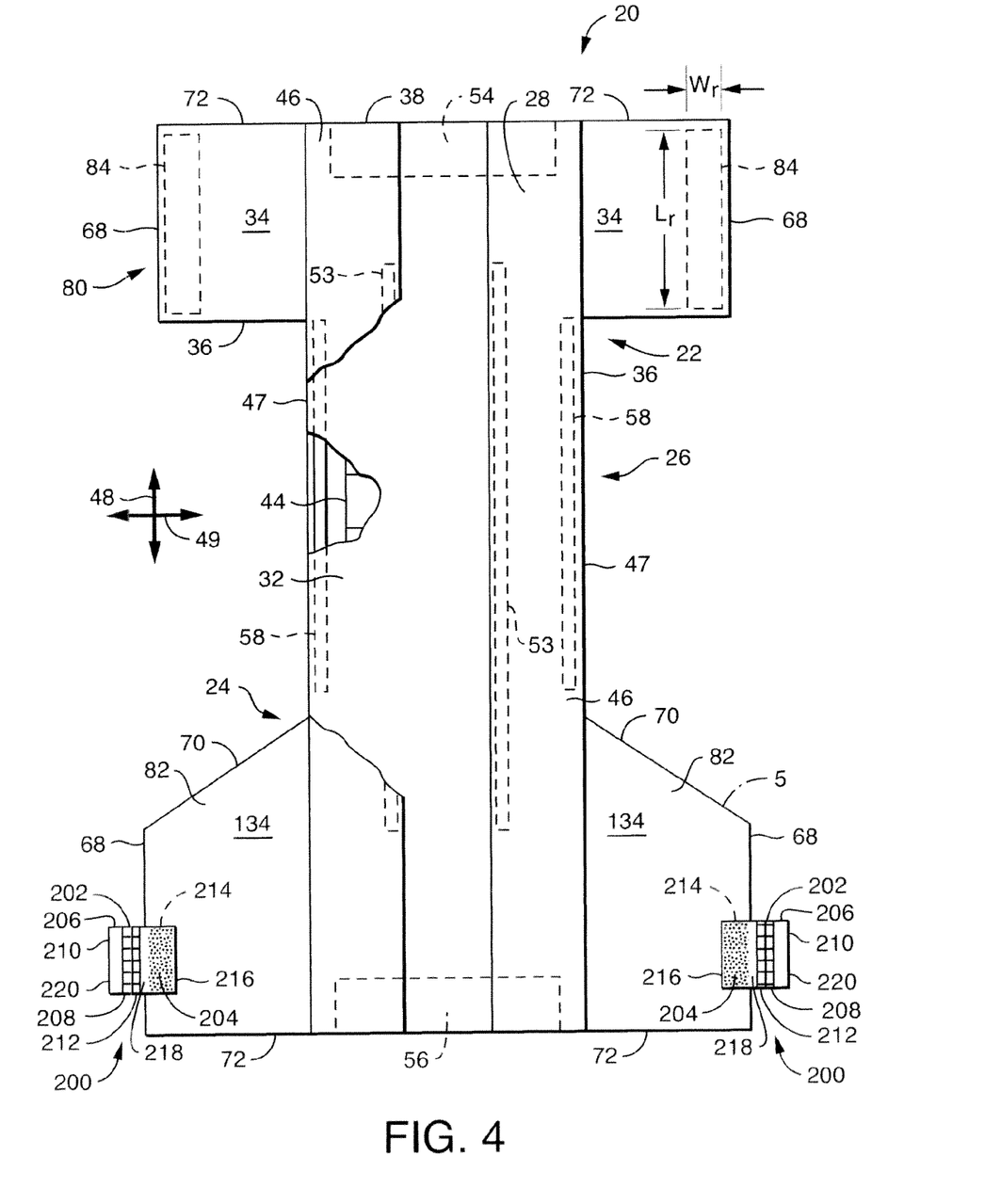
FIG. 4 is a top plan view similar to FIG. 3 showing the surface of the training pants that faces the wearer when worn and with portions cut away to show underlying features.

The illustrated pants 20 includes a central absorbent assembly, generally indicated at 32, which when laid flat as in FIGS. 3 and 4 can be rectangular or any other desired shape. A pair of laterally opposite front side panels 34 extends outward from the absorbent assembly 32 at the front waist region 22 (thereby forming transversely outer portions of the front waist region, and more broadly in part forming transversely opposite sides of the training pants). Laterally opposite back side panels 134 extend outward from the absorbent assembly 32 at the back waist region 24 (thereby forming transversely outer portions of the back waist region, and together with the front side panels 34 further defining the sides of the pants).

The central absorbent assembly 32 of the illustrated aspect includes an outer cover 40 and a bodyside liner 42 (FIGS. 1 and 2) connected to the outer cover in a superposed relation by suitable means such as adhesives, ultrasonic bonds, thermal bonds or other conventional techniques. An absorbent structure 44 (FIG. 4) is disposed between the outer cover and the bodyside liner. A pair of containment flaps 46 (FIG. 4) is secured to the bodyside liner 42 for inhibiting the lateral flow of body exudates. The central absorbent assembly 32 has opposite ends which form portions of the front and back waist edges 38 and 39, and opposite side edges 47 which form portions of the side edges 36 of the training pants 20 (FIGS. 3 and 4).

The absorbent assembly 32 and side panels 34, 134 can include two or more separate elements, as shown in FIGS. 1 and 2, or they can be integrally formed. Integrally formed side panels 34, 134 and absorbent assembly 32 would include at least some common materials, such as the bodyside liner, flap composite, outer cover, other materials and/or combinations thereof, and could define a one-piece elastic, stretchable, or nonstretchable pants 20. For further reference, arrows 48 and 49 in FIGS. 3 and 4 depict the orientation of a longitudinal axis and a transverse or lateral axis, respectively, of the training pants 20.

With the training pants 20 in the fastened condition as illustrated fully in FIG. 1 and partially in FIG. 2, the front and back side panels 34, 134 are attached to each other by a primary, or article fastening system 80 to define the pre-assembled three-dimensional wear configuration of the pants, having a waist opening 50 and a pair of leg openings 52. The front waist region 22 includes the portion of the training pants 20 which, when worn, is positioned at least in part on the front of the wearer while the back waist region 24 includes the portion of the training pants which is positioned at least in part on the back of the wearer. The crotch region 26 of the training pants 20 includes the portion of the training pants 20 which is positioned between the legs of the wearer and covers the lower torso of the wearer.

The front and back side panels 34 and 134 include the portions of the training pants 20 (and more particularly of the front and back waist regions 22, 24) which, when worn, are positioned on the hips of the wearer. The attached side panels 34, 134 thus broadly define the transversely opposite sides of the pants 20 at an engagement seam 66 along which the fastening system 80 releasably attaches the front and back side panels. The waist edges 38 and 39 of the training pants 20 are configured to encircle the waist of the wearer and together define the waist opening 50 (FIG. 1). Portions of the side edges 36 in the crotch region 26 generally define the leg openings 52.

The central absorbent assembly 32 is configured to contain and/or absorb exudates discharged from the wearer. For example, the containment flaps 46 are configured to provide a barrier to the transverse flow of body exudates. A flap elastic member 53 (FIG. 4) can be operatively joined with each containment flap 46 in any suitable manner as is well known in the art. The elasticized containment flaps 46 define a partially unattached edge which assumes an upright configuration in at least the crotch region 26 of the training pants 20 to form a seal against the wearer's body. The containment flaps 46 can be located along the side edges 36 of the pants 20, and can extend longitudinally along the entire length of the absorbent assembly 32 or can only extend partially along the length of the absorbent assembly. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 also suitably includes a front waist elastic member 54 (FIG. 4), a rear waist elastic member 56, and leg elastic members 58, as are known to those skilled in the art. The waist elastic members 54 and 56 can be attached to the outer cover 40 and/or the bodyside liner 42 along the opposite waist edges 38 and 39, and can extend over part or all of the waist edges. The leg elastic members 58 can be attached to the outer cover 40 and/or the bodyside liner 42 along the opposite side edges 36 and positioned in the crotch region 26 of the training pants 20. The leg elastic members 58 can be longitudinally aligned along each side edge 47 of the absorbent assembly 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 include a plurality of dry-spun coalesced multifilament spandex elastomeric threads sold under the trade name LYCRA® and available from E.I. Du Pont de Nemours and Company, Wilmington, Del., U.S.A.

The outer cover 40 suitably includes a material which is substantially liquid impermeable. The outer cover 40 can be a single layer of liquid impermeable material, but more suitably includes a multi-layered laminate structure in which at least one of the layers is liquid impermeable. For instance, the outer cover 40 can include a liquid permeable outer layer and a liquid impermeable inner layer that are suitably joined together by a laminate adhesive, ultrasonic bonds, thermal bonds, or the like. Suitable laminate adhesives can be applied continuously or intermittently as beads, a spray, parallel swirls, or the like. The liquid permeable outer layer can be any suitable material and is desirably one that provides a generally cloth-like texture. The outer layer can also be made of those materials of which the liquid permeable bodyside liner 42 is made. While it is not a necessity for the outer layer to be liquid permeable, it is suitable that it provides a relatively cloth-like texture to the wearer.

The inner layer of the outer cover 40 can be both liquid and vapor impermeable, or it can be liquid impermeable and vapor permeable. The inner layer can be manufactured from a thin plastic film, although other flexible liquid impermeable materials can also be used. The inner layer, or the liquid impermeable outer cover 40 when a single layer, prevents waste material from wetting articles, such as bed sheets and clothing, as well as the wearer and caregiver.

If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. One suitable "breathable" material is composed of a microporous polymer film or a nonwoven fabric that has been coated or otherwise treated to impart a desired level of liquid impermeability.

It is also contemplated that the outer cover 40 can be stretchable, and more suitably elastic. In particular, the outer cover 40 is suitably stretchable and more suitably elastic in at least the transverse or circumferential direction of the pants 20. In other aspects the outer cover can be stretchable, and more suitably elastic, in both the transverse and the longitudinal direction.

The liquid permeable bodyside liner 42 is illustrated as overlying the outer cover 40 and absorbent core 44, and can, but need not, have the same dimensions as the outer cover 40. The bodyside liner 42 is suitably compliant, soft feeling, and non-irritating to the child's skin. Further, the bodyside liner 42 can be less hydrophilic than the absorbent structure 44 to present a relatively dry surface to the wearer and permit liquid to readily penetrate through its thickness. Alternatively, the bodyside liner 42 can be more hydrophilic or can have essentially the same affinity for moisture as the absorbent structure 44 to present a relatively wet surface to the wearer to increase the sensation of being wet. This wet sensation can be useful as a training aid. The hydrophilic/hydrophobic properties can be varied across the length, width and/or depth of the bodyside liner 42 and absorbent structure 44 to achieve the desired wetness sensation or leakage performance.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42.

For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. The surfactant can be applied by any conventional means, such as spraying, printing, brush coating or the like. The surfactant can be applied to the entire bodyside liner 42 or can be selectively applied to particular sections of the bodyside liner, such as the medial section along the longitudinal center line.

The bodyside liner 42 can also be stretchable, and more suitably elastic. In particular, the bodyside liner 42 is suitably stretchable and more suitably elastic in at least the transverse 49, or circumferential direction of the pants 20. In other aspects, the bodyside liner 42 can be stretchable, and more suitably elastic, in both the transverse 49 and the longitudinal 48 directions.

As noted previously, the illustrated training pants 20 have front and back side panels 34 and 134 defining transversely opposite sides of the pants in the wear configuration of the pants. The side panels 34, 134 can be permanently attached along seams 66 to the central absorbent assembly 32 in the respective front and back waist regions 22 and 24. More particularly, as seen best in FIGS. 2 and 3, the front side panels 34 can be permanently attached to and extend transversely outward beyond the side edges 47 of the absorbent assembly 32 in the front waist region 22, and the back side panels 134 can be permanently attached to and extend transversely outward beyond the side edges of the absorbent assembly in the back waist region 24. The side panels 34 and 134 can be attached to the absorbent assembly 32 using attachment means known to those skilled in the art such as adhesive, thermal, pressure or ultrasonic bonding. Alternatively, the side panels 34 and 134 can be formed as an integral portion of a component of the absorbent assembly 32. For example, the side panels can include a generally wider portion of the outer cover 40, the bodyside liner 42, and/or another component of the absorbent assembly 32.

The front and back side panels 34, 134 each have an outer edge 68 spaced laterally from the seam 66, a leg end edge 70 disposed toward the longitudinal center of the training pants 20, and a waist end edge 72 disposed toward a longitudinal end of the training pants. The leg end edge 70 and waist end edge 72 extend from the side edges 47 of the absorbent assembly 32 to the outer edges 68. The leg end edges 70 of the side panels 34 and 134 form part of the side edges 36 of the training pants 20. The leg end edges 70 of the illustrated aspect are suitably curved and/or angled relative to the transverse axis 49 to provide a better fit around the wearer's legs. However, it is understood that only one of the leg end edges 70 can be curved or angled, such as the leg end edge of the back waist region 24, or neither of the leg end edges can be curved or angled, without departing from the scope of this invention. The waist end edges 72 are suitably parallel to the transverse axis 49. The waist end edges 72 of the front side panels 34 form part of the front waist edge 38 of the training pants 20, and the waist end edges 72 of the back side panels 134 form part of the back waist edge 39 of the pants.

The side panels 34, 134 suitably, although not necessarily, include a stretchable material capable of stretching in a direction generally parallel to the transverse axis 49 of the training pants 20. More suitably the side panels 34, 134 include an elastic material. Suitable elastic materials, as well as one process of incorporating stretchable side panels into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the stretch material can include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference.

In one particularly suitable aspect, at least the front side panels 34 and more suitably both the front and back side panels 34, 134 include a vertical filament laminate (VFL) material. A VFL is a composite material having at least one gatherable layer such as a non-woven material and at least one elastic layer. The layers are joined together when the elastic layer is extended from its original condition so that upon relaxing the layers, the gatherable layer is gathered. The composite can be stretched to the extent that the non-elastic material gathered between the bond locations allows the elastic material to elongate. One type of vertical filament laminate is disclosed, for example, by U.S. Pat. No. 6,916,750 to Thomas et al., the content of which is incorporated herein by reference in its entirety. More suitably, the front and back side panels include a VFL in which two non-woven (gatherable) layers sandwich an elastic layer so that both faces of the VFL are gatherable. The rugosities formed in the gatherable layers of such a VFL material allow the VFL material to be used as a loop component of a fastening system.

Alternatively, the side panel material can include other woven or nonwoven materials, such as those described above as being suitable for the outer cover 40 or bodyside liner 42; mechanically pre-strained composites; or stretchable but inelastic materials.

The absorbent structure 44 can be any structure which is generally compressible, conformable, non-irritating to the wearer's skin and capable of absorbing and retaining liquid body exudates, and can be manufactured in a wide variety of sizes and shapes, and from a wide variety of absorbent materials commonly used in the art. For example, the absorbent structure 44 suitably includes a matrix of absorbent fibers, and more particularly hydrophilic fibers, such as a web of cellulosic fluff. In a particularly suitable aspect, the absorbent structure 44 includes a matrix of cellulosic fluff, such as wood pulp fluff, and superabsorbent particles. The wood pulp fluff can be exchanged with synthetic, polymeric, meltblown fibers or short cut homofil bicomponent synthetic fibers and natural fibers. The superabsorbent particles can be substantially homogeneously mixed with the hydrophilic fibers or can be nonuniformly mixed. The fluff and superabsorbent particles can also be selectively placed into desired zones of the absorbent structure 44 to better contain and absorb body exudates. The concentration of the superabsorbent particles can also vary through the thickness of the absorbent core 44. Alternatively, the absorbent structure 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany.

In one aspect, the absorbent structure 44 includes a blend of wood pulp fluff and superabsorbent material. As a general rule, the superabsorbent material is present in the absorbent structure 44 in an amount of from 0 to about 90 weight percent based on total weight of the absorbent assembly. The absorbent structure 44 suitably has a density within the range of about 0.10 to about 0.35 grams per cubic centimeter. The absorbent structure 44 can be wrapped or encompassed by a suitable wrap that can help maintain the integrity and/or shape of the absorbent assembly.

The article fastening system 80 includes laterally opposite first article fastening components 82 adapted for refastenable engagement to corresponding second article fastening components 84. In one aspect, a front or outer surface of each of the article fastening components 82, 84 includes a plurality of engaging elements. The engaging elements of the first article fastening components 82 are adapted to repeatedly engage and disengage corresponding engaging elements of the second article fastening components 84 to releasably secure the pants 20 in its three-dimensional configuration. The article fastening system 80 provides an attachment of a strength sufficient to maintain the article in a wear configuration during use of the pants 20 by the wearer.

The article fastening components 82, 84 can include any refastenable fasteners suitable for absorbent articles, such as adhesive fasteners, cohesive fasteners, mechanical fasteners, or the like. In particular aspects, the article fastening components 82, 84 include mechanical fastening components for improved performance. Suitable mechanical fastening components can be provided by interlocking geometric shaped materials, such as hooks, loops, bulbs, mushrooms, arrowheads, balls on stems, male and female mating components, buckles, snaps, or the like.

In the illustrated aspect, the first article fastening components 82 (i.e., one on each side of the training pants 20) include loop fasteners and the second article fastening components 84 include complementary hook fasteners. Alternatively, the first article fastening components 82 can include hook fasteners and the second article fastening components 84 can include complementary loop fasteners. In another aspect, the article fastening components 82, 84 can include interlocking similar surface fasteners, or adhesive and cohesive fastening elements such as an adhesive fastener and an adhesive-receptive landing zone or material; or the like. Although the training pants 20 illustrated in FIG. 1 show the back side panels 134 overlapping the front side panels 34 upon connection thereto, which is convenient, the training pants 20 can also be configured so that the front side panels overlap the back side panels when connected. One skilled in the art will recognize that the shape, density and polymer composition of the hooks and loops can be selected to obtain the desired level of engagement between the article fastening components 82, 84. A more aggressive hook material can include a material with a greater average hook height and/or a greater percentage of directionally-aligned hooks. When engaged, the article fastening components 82, 84 of the illustrated aspect define the refastenable engagement seams 66 (FIG. 2).

As discussed above, in one particularly suitable aspect, as best seen in FIGS. 2 and 4, the back side panels 134 are constructed so that the inner surfaces of the respective back side panels define loop article fastening components 82 (i.e., the back side panels 134 and the article fastening components 82 are formed integrally). It is understood, however, that the loop article fastening components 82 can be formed separate from the back side panels 134 and attached thereto, such as by adhesive, thermal bonds, ultrasonic bonds, pressure bonds or other suitable techniques without departing from the scope of this invention.

With particular reference now to FIGS. 1 and 2, a secondary, or disposal fastening system, generally indicated at 200, is provided for use in securing the training pants 20 in a compact disposal configuration (FIG. 6) described in further detail later herein. As illustrated in FIGS. 2 and 4, the disposal fastening system includes a tab 202 attached to each of the back side panels 134 (broadly, to the transversely opposite sides of the training pants 20) and extending in part transversely outward of the respective back side panels for opposed relationship with the corresponding front side panels in the wear configuration of the pants. As seen best in FIG. 2, each disposal tab 202 includes an attachment region 204 at which the disposal tab 202 is attached to the respective back side panel 134, and a tab region 206 extending transversely outward from the attachment region 204. More suitably, the tab region 206 of the disposal tab 202 includes at least one tab fastener region 208 having a tab fastening component 212 for use in securing the pants 20 in their compact disposal configuration, and can further include a grip region 210 transversely outward of the tab fastener region 208 for use in manually gripping and manipulating the disposal tab 202 relative to the pants 20.

The tab region 206 via its fastener region 208 can be releasably attached to a side panel when the pants 20 is in a wear configuration. Such a releasable attachment by the tab region 206 alone, however, provides an attachment strength that is insufficient to maintain the pants 20 in a wear configuration during use of the pants 20 by the wearer.

The attachment region 204 has an attachment width, which is the longitudinal width of the disposal tab 202 in the attachment region 204. The tab region 206 has a gripping width, which is the longitudinal width of the disposal tab 202 in the tab region 206. In one aspect of the present disclosure, the disposal tab 202 is substantially rectilinear, and more specifically rectangular, with one or more orthogonal corners 220 and with the attachment width substantially equal to the gripping width. If present, at least one orthogonal corner 220 should be disposed distally from attachment region 206. This rectilinear arrangement allows the greatest amount of gripping area in conjunction with the most efficient use of material because the rectilinear shape of the disposal tab 202 allows the disposal tab 202 to be cut from a sheet or a roll with little to no loss of material, particularly in view of the material waste inherent in a more arcuate or sinusoidal tab shape. In addition, the rectilinear shape of the disposal tab 202 allows for easier registered placement of the disposal tab 202 in a high-speed manufacturing process. Also, the rectilinear shape of the disposal tab 202 allows a wearer or caregiver to easily access and lift the tab region 206 of the disposal tab 202 that is otherwise releasably attached to the pants 20. The corners allow easier access to lift the tab than an acutely-shaped tab. Finally, the rectilinear shape of the disposal tab 202 reduces the likelihood of the disposal tab 202 being torn from the pants 20 during use, readjustment, or disposal of the pants 20.

Disposable articles with an improved means of disposal and removal such as those described herein can provide greater convenience for the wearer or caregiver. The disposal tab 202 can have multiple functions including as a disposal securing mechanism, as a grasping point for opening the side seam, as a grasping point for pulling the pants on, and as a zone of increased engagement at the side seam, or as any combination of these.

The tab fastening component 212 of the illustrated tab fastener region 208 includes a hook fastener. The outer surface of each front side panel 34 suitably defines a corresponding fastening component, e.g., a loop fastener, to permit the disposal tab 202 on each side of the pants 20 to be attached at its tab fastener region 208 to the respective front side panel (i.e., broadly, to the pants 20) in the wear configuration of the pants 20. For example, the front side panel 34 in one particularly suitable aspect can be constructed of VFL material as described previously so that the outer surface of the front side panel 34 itself defines a loop fastening component. Alternatively, a loop fastener component (not shown) can be formed separately from the front side panel 34 and attached to the panel outer surface without departing from the scope of this invention. The outer facing surface 30 of the outer cover 40 of the pants 20 is also suitably constructed to define a loop fastener, such as by forming the outer cover of a material that defines a loop fastening component (e.g., VFL or other suitable material) or by forming a separate loop fastening component and attaching it to the outer surface of the pants outer cover, to permit attachment of the disposal tab 202 to the outer cover in the disposal configuration of the pants 20.

It is understood that the tab fastening component(s) 212 defining the one or more tab fastener regions 208 of the disposal tab 202 can instead be a loop fastener component, with the outer surfaces of the front side panels 34 and outer cover 40 of the pants 20 being constructed to define corresponding hook fastening components. In other aspects, the tab fastening component 212 defining the tab fastener region(s) 208 and the outer surfaces of the front side panels 34 and pants outer cover 40 can include other suitable releasably attachable fasteners without departing from the scope of this invention. It is also contemplated that the tab fastening component 212 defining the tab fastener region 208 can be releasably attachable to the pants 20 (e.g., to the front side panel 34) in the wear configuration but otherwise more permanently attachable elsewhere on the pants (e.g., to the outer cover 40) in the disposal configuration of the pants. The term permanent attachment is intended herein to refer to an attachment that is generally not releasable without some damage or substantially reduced ability to reattach to the fastening component and/or the component to which the fastening component is attached.

In one alternative aspect, the tab region 206 of the disposal tab 202 includes at least one gap region 218 between the attachment region 204 and the tab fastener region 208 to allow for manufacturing tolerances in preventing the tab fastening component 212 from being attached to the side panel. In other words, the gap region 218 allows the tab fastener region 208 to be free from bonding to the pants 20. Such an arrangement further reduces the opportunity for hook-on-hook interface between the tab fastening component 212 and the article fastening system 80.

In another alternative aspect, the disposal tab 202 can be printed, embossed, or otherwise emblazoned such that the visible portion has the appearance of a garment tag or label. Design elements, such as a label appearance, can communicate branding, sizing, or other features, and/or can be integrated with the overall design of the pants 20. The effect of such a disposal tab design scheme can be enhanced by the rectangular shape of the disposal tab 202 because such a shape enhances the garment-like appearance of the pants 20. Design options for the label include, but are not limited to, digital printing which would allow each label to be different, use of special inks such as a thermographic or puffy ink that allows for a raised, grippy surface for ease of use, novelty inks such as glitter ink, and the like.

In still another alternative aspect of the present disclosure, a disposal tab 202 of the type described herein can be folded back upon itself at or near the gap region 218 such that the tab region 204 partially or completely overlies the attachment region 206. In this aspect, the tab fastening component 212 can be in a face-to-face arrangement with the attachment region 206 and can engage the attachment region 206 if the attachment region 206 is manufactured from a mechanical fastening material that is engageable with the tab fastening component 212. For example, the attachment region 206 can engage with the tab fastening component 212 if one is of a hook-type material and the other is of a loop-type material. In one aspect, such folding is to be performed prior to the attachment of the refastenable seam 66. As such, all or part of the folded disposal tab 202 can be captured between the front and back side panels 34, 134.

If in its final arrangement the folded disposal tab 202 is entirely inboard of an edge of a front or back side panel 34, 134, then the folded disposal tab 202 will be hidden when the pants 20 is in a wear configuration. In this aspect, the disposal tab 202 can be used for a disposal configuration by separating the refastenable seam 66, unfolding the disposal tab 202, and configuring the pants 20 for disposal as descried herein. If in its final arrangement the folded disposal tab 202 is not entirely inboard of an edge of a front or back side panel 34, 134, and a portion of the folded disposal tab 202 extends beyond an edge of a front or back side panel 34, 134, the disposal tab 202 will be partially hidden but still available as a finger tab as described herein.

In these aspects, if the side of the disposal tab 202 opposite the side including the tab fastening component 212 includes a complementary engaging material, one of the article fastening components 82, 84 can also engage the folded disposal tab 202 when it engages the other of the article fastening components 82, 84. For example, if the side of the disposal tab 202 opposite the side including the tab fastening component 212 includes a loop-type material, then the one of the article fastening components 82, 84 that includes hook-type material can engage the folded disposal tab in addition to the loop-type material of the other of the article fastening components 82, 84.

In the illustrated aspect, the disposal tabs 202 attach to the outer surfaces of the front side panels 34 (e.g., outer surface 30 of pants 20) in the wear configuration of the article. It is contemplated that in the wear configuration the disposal tabs 202 can be configured to attach to the inner surfaces of the front side panels 34 (e.g., inner surface 28 of pants 20) and remain within the scope of this invention.

The attachment region 204 of each disposal tab 202 is suitably attached to the respective back side panel 134 (broadly, to the respective side of the pants 20) and in the illustrated aspect is attached to the inner surface of the back side panel. It is understood, however, that the attachment region 204 can instead be attached to the outer surface of the back side panel 134. The attachment region 204, in the aspect in which the back side panel 134 overlaps the front side panel 34, is more suitably attached to the back side panel adjacent the transverse edge of the back side panel. But the attachment region 204 can instead be attached to the back side panel 134 more transversely distal from the transverse edge of the back side panel, such as when the front side panel 34 overlaps the back side panel, without departing from the scope of this invention.

The attachment region 204 of each disposal tab 202 is suitably attached to the inner surface of the back side panel 134, such as by adhesive, thermal bonding, ultrasonic bonding, pressure bonding, or other suitable attachment technique. More suitably, an attachment face 214 (FIG. 4) of each disposal tab 202 is attached to the inner surface of the back side panel 134 at the attachment region 204 of the tab. The tab region 206 of each disposal tab 202 extends transversely outward of the attachment region 204 into overlapping or opposed relationship with the outer surface of the corresponding front side panel 34 so that the tab region is accessible exterior of the pants 20 in the wear configuration of the pants. It is understood, however, that the tab region 206 can instead be in opposed relationship with and releasably attachable to the inner surface of the front side panel 34 without departing from the scope of this invention.

In another aspect, the tab region 206 of each disposal tab 202 is suitably positioned generally longitudinally offset along the length of the side of the pants 20 (e.g., between the waist opening 50 and respective leg opening 52), and in particular at the engagement seam 66 between the front and back side panels 34, 134. More suitably, the tab region 206 has a transversely extending centerline disposed within about 8 cm from the waist opening 50 along the length of the side of the pants 20, and in particular at the engagement seam 66, and even more suitably within about 5 cm from the waist opening 50 along the length at the engagement seam 66, and still more suitably within about 2 cm from the waist opening 50 along the length at the engagement seam 66. For processing ease and aiding performance attributes associated with the disposal tab 202, the disposal tab 202 is positioned at least 5 mm from the waist opening 50 of the pants 20.

The tab fastener region 208 of each disposal tab 202 suitably extends lengthwise of the tab, within the tab region 206 thereof, to the edges of the disposal tab 202 at the tab region 206. It is understood, however, that the fastener region 208 need not extend the full length of the disposal tab 202 at the tab region 206 to remain within the scope of this invention.

When the disposal tab 202 includes a grip region 210 such as in the illustrated aspect of FIGS. 1-4, the disposal tab 202 is suitably constructed so that the grip region 210 is non-attachable to the pants 20, at least in the wear configuration of the pants 20. The term non-attachable as used in this instance means that the grip region 210 is not releasably or otherwise removably attachable to the pants 20 in the wear configuration thereof, nor is the grip region 210 permanently attached to the pants 20. In one aspect, the grip region 210 extends transversely outward from the tab fastener region 208 of each disposal tab 202 a distance of at least about 1 mm, such as in the range of about 1 mm to about 10 mm to provide sufficient unattached material of the tab for readily gripping and pulling on the tab.

In one aspect, each disposal tab 202 is suitably constructed of a base substrate 216 having a tab fastening component 212 (e.g., a hook fastening component in the illustrated aspect) attached thereto such as by adhesive bonding, thermal bonding, ultrasonic bonding, pressure bonding, or other suitable technique to define the tab fastener region 208 of the disposal tab 202. In certain aspects, the base substrate 216 can be constructed such that, other than the fastener region 208, the disposal tab 202 is not releasably attachable to the pants 20, particularly at the grip region 210 (if provided) of the disposal tab 202. In one particularly suitable aspect, the base substrate 216 is less stretchable (at least in the transverse direction thereof) than the pants 20 (in the transverse, or circumferential direction thereof) and more suitably the base substrate is non-stretchable so that pulling on the tab transversely of pants 20 to secure the pants 20 in their disposal configuration the pants 20 (and in particular the back side panels 134) are allowed to stretch. As an example, one suitable material from which the base substrate 216 can be constructed is a three-layer nonwoven polypropylene material known as SMS. SMS is an acronym for Spunbond-Meltblown-Spunbond, the process by which the three layers are constructed and then laminated together. One example of an SMS material is described in U.S. Pat. No. 4,041,203 to Brock et al. It should be noted, however, that other nonwovens as well as other materials including wovens, films, foam/film laminates and combinations thereof can be used to construct the disposal tab 202 without departing from the scope of this invention.

In particular aspects, the base substrate 216 is constructed of a material that is releasably attachable with the article fastener component 84 of the article fastening system 80. For example, in particular aspects, the base substrate 216 is formed from a material such as acrylic, polyamide, polyethylene, polypropylene or polyester, and is formed into a "loop"-type material by methods such as warp knitting, stitch bonding or needle punching. The base substrate 216 can include any fibrous structure capable of entangling or catching hook materials, such as carded, spunbonded or other nonwoven webs or composites, including elastomeric and nonelastomeric composites. One material suitable for use as a base substrate 216 is available from Guilford Mills, Inc., Greensboro, N.C., U.S.A. under the trade designation No. 36549. Another suitable base substrate material includes a pattern un-bonded web as disclosed in co-assigned U.S. Pat. No. 5,858,515 issued Jan. 12, 1999 to Stokes, et al., which is incorporated herein by reference to the extent consistent herewith. In particular aspects, the base substrate 216 can include a "loop"-type material as just discussed but that is attached to a backing structure, and the composite is then attached to the pants 20, such as along the side edges of the front or back side panels 34, 134.

As previously discussed, in particular aspects each of the transversely opposite sides of the pants 20 include a material (such as, for example, a nonwoven material) that is releasably engageable with the hook material of the primary fastening system. When the article is fastened in the wear configuration, it is possible in certain aspects that the hook material of article fastening system 80 simultaneously engages both the disposal-tab base substrate 216 and an outer facing of the transversely opposite sides of the article (such as, for example, the outermost nonwoven facing of an elastomeric nonwoven laminate). For example, if the greatest length of the attachment region 204 of the disposal tab 202 is less than the greatest length of the engagement seam, it is probable that the refastenable seam 66 will be formed not only by engagement of the hook component to the base substrate 216, but also by engagement of the hook component to portions of the outer facing of the side panel 134 that extend beyond the longitudinal ends of the attachment region 204 of the disposal tab 202.

Similarly, if the greatest width of the attachment region 204 of the disposal tab 202 is less than the greatest width of the engagement seam, it is probable that the refastenable seam 66 will be formed not only by engagement of the hook component to the base substrate 216, but also by engagement of the hook component to portions of the outer facing of the side panel 134 that extend transversely inward of the longitudinal side edge of the attachment region 204 of the disposal tab 202, as representatively illustrated in FIG. 1. However, it is not necessary that the hook material of the article fastening system 80 simultaneously engage both the disposal-tab base substrate 216 and the transversely opposite sides of the article. For example, if the greatest length of the attachment region 204 of the disposal tab 202 is greater than the greatest length of the engagement seam, and/or if the greatest width of the attachment region 204 of the disposal tab 202 is greater than that the greatest width of the engagement seam, the refastenable seam 66 can be formed solely by engagement of the hook component to the base substrate 216.

In use, the training pants 20 are constructed and pre-assembled in their wear configuration, with the article fastening system 80 releasably attaching the front and back waist regions 22, 24 (and more particularly the front and back side panels 34, 134 in the illustrated aspect). The tab fastener region 208 of each disposal tab 202 is releasably attached to the outer surface of the respective front side panel 34 to releasably attach the tab region 206 of each disposal tab 202 to the pants 20 in the wear configuration of the pants 20.

When the pants 20 are to be discarded after use, the pants 20 can be slipped off of the wearer in the manner of conventional underpants, or the front and back waist regions 22, 24 can be detached from each other (e.g., by separation of the article fastening components 82, 84 of the article fastening system 80) and the pants 20 removed from the wearer. Where the front and back waist regions 22, 24 are separated to remove the pants 20, the tab fastener regions 208 of the disposal tabs 202 must be detached from the front waist region (e.g., from the front side panels 34). To detach the tab fastener regions 208 of the disposal tabs 202 illustrated in the aspect of FIGS. 1-4, the grip region 210 of each disposal tab 202 is gripped between the thumb and forefinger and pulled away from the front side panel 34 until the tab fastener region 208 breaks free from its attachment to the front side panel 34.

Figure 5:
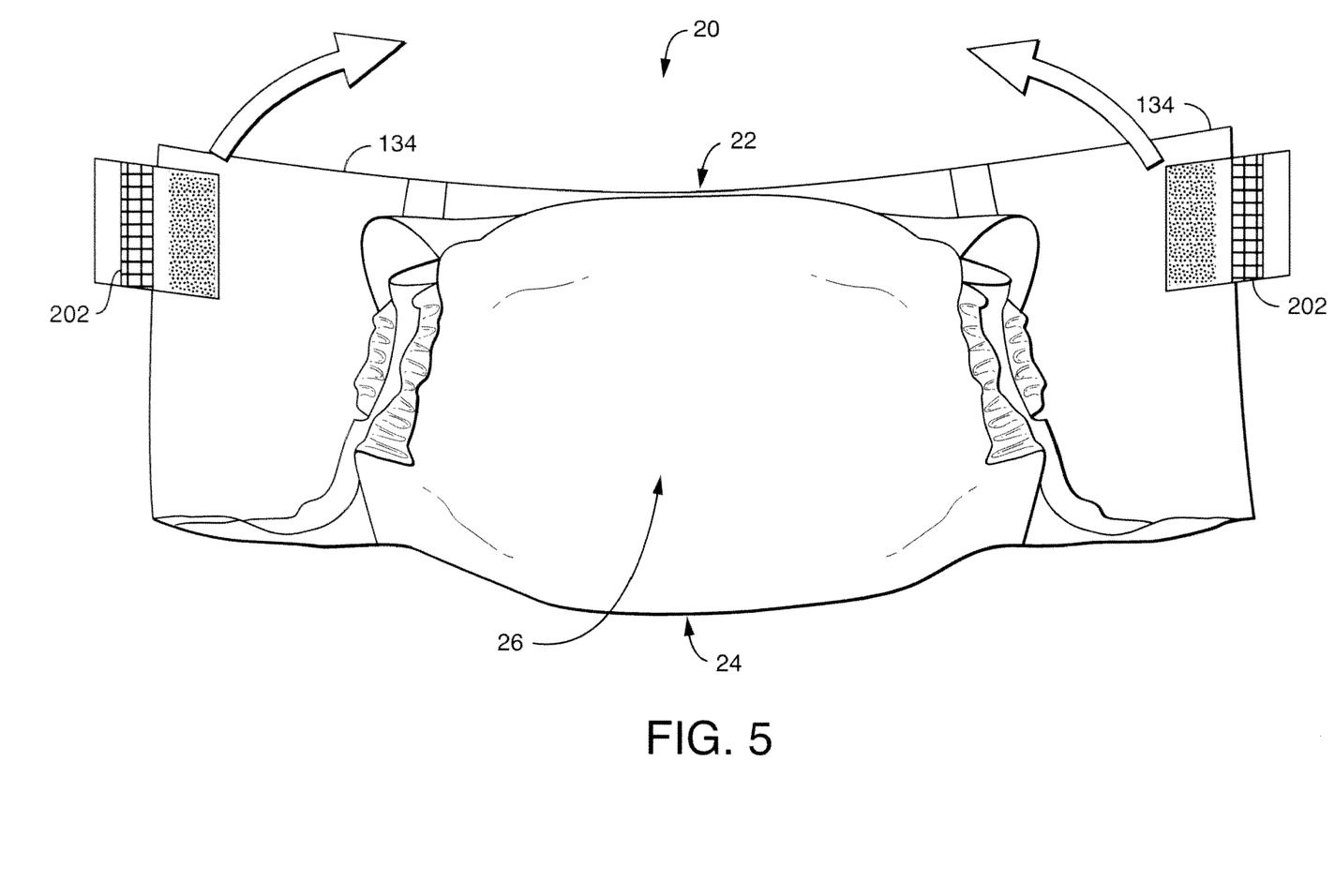
FIG. 5 is a schematic of the training pants of FIG. 1 in a partially compacted discard configuration.

To dispose of the used pants 20, the pants 20 are laid on a surface with the back waist region 24 down against the surface and with the front and back waist regions 22, 24 in opposed relationship with each other. The sides, and more particularly the front and back side panels 34, 134 in the illustrated aspect, suitably extend transversely outward in opposed relationship with each other. With reference to FIG. 5, the crotch region 26 and a portion of the back waist region 24 of the pants 20 are then folded or rolled up over the front waist region 22 of the pants. If not already done, the tab regions 206 of the disposal tabs 202 are gripped at the grip regions 210 thereof and are pulled away from the pants 20 to detach the tab regions 206 from the pants 20 (i.e., from the front side panels 34 in the illustrated aspect). While gripping the detached tab regions 206 of the disposal tabs 202, the tab regions 206 are pulled around the folded or rolled portion of the pants 20 and then toward each other as indicated by the direction arrows in FIG. 5.

Figure 6:
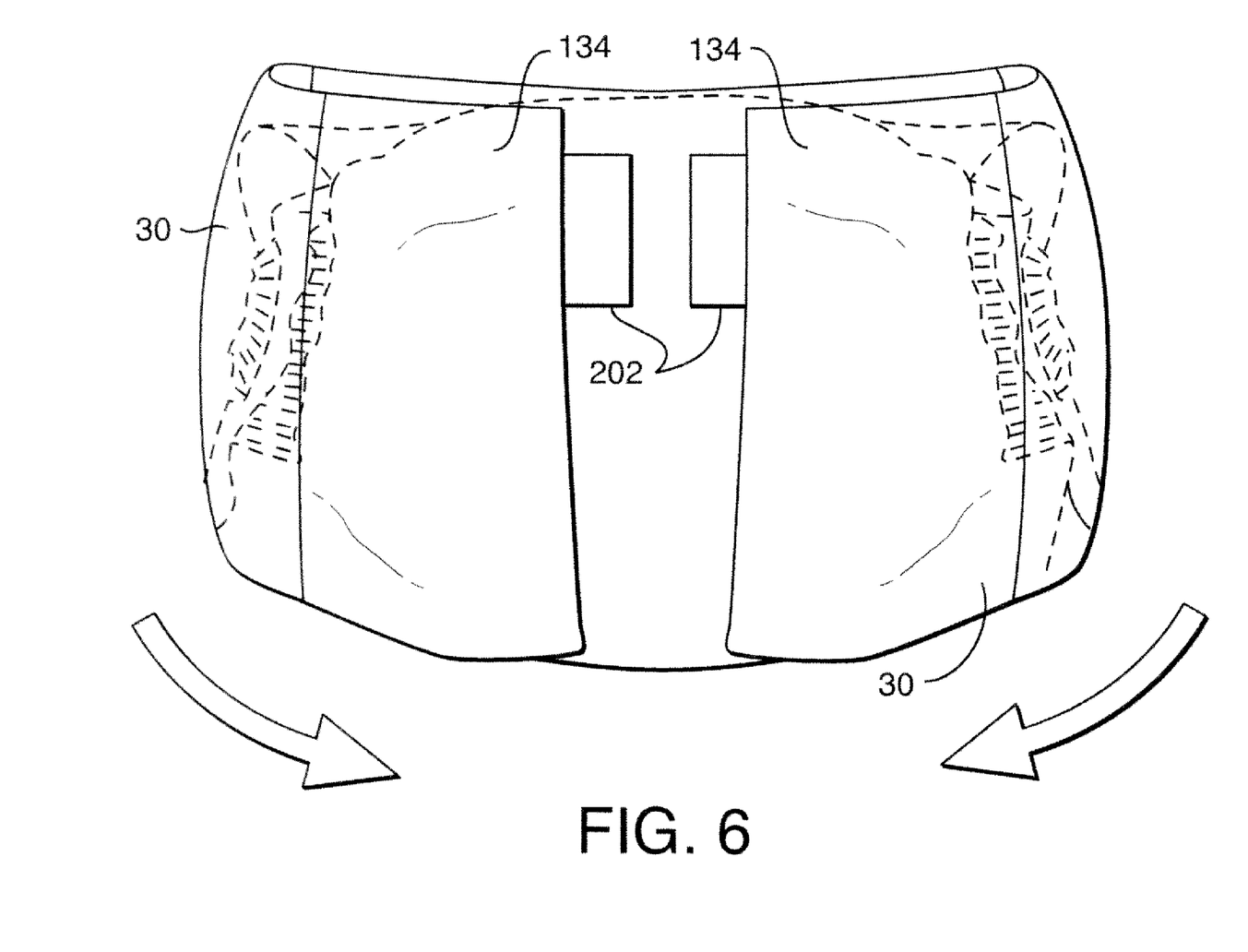
FIG. 6 is a schematic of the training pants of FIG. 5 in a fully compacted discard configuration with the disposal fastening system in a fastened condition to secure the pants in the discard configuration.

Pulling on the disposal tabs 202 in this manner pulls on and suitably stretches the stretchable back waist region 24 (and more particularly the stretchable back side panels 134 in the illustrated aspect) so that the back waist region 24 and more suitably the back side panels 134 substantially surround the folded or rolled portion of the pants 20. The tab fastener regions 208 of the disposal tabs 202 are attached to the folded or rolled portion of the pants 20 (i.e., to the outer surface 30 of the pants) to thereby secure the pants in their compact disposal configuration as illustrated in FIG. 6. Pulling on and stretching the back waist region 24 of the pants 20 to surround the folded or rolled portion also places in tension (e.g., due to the elasticity in the elastic back side panels 134) a substantial transverse or circumferential segment of the circumscribing portion of the pants 20 (e.g., the back waist region 24 and more particularly the back side panels 134 in the illustrated aspect) in the disposal configuration of the pants 20. This allows the pants 20 to be relatively compact in the disposal configuration and to be held generally tightly in this compact configuration to reduce the risk of leakage from the pants.

While in FIG. 6 the disposal tabs 202 are brought into positions generally adjacent each other to secure the pants 20 in the disposal configuration thereof, it is contemplated that one of the disposal tabs 202 can be pulled across the longitudinal centerline of the pants 20 and secured thereto (e.g., to the outer surface 30 of the pants), and then the other disposal tab 202 pulled across the longitudinal centerline over and beyond the one disposal tab 202 and secured to the pants 20, such as the back side panel 134 to which the one disposal tab 202 is attached since it is of a VFL material, to provide a further compacted disposal configuration of the pants 20.

When introducing elements of the present invention or the preferred aspect(s) thereof, the articles "a", "an", "the", and "the" are intended to mean that there are one or more of the elements. The terms "comprising," "including", and "having" are intended to be inclusive and mean that there can be additional elements other than the listed elements.

The disclosure has been described with reference to various specific and illustrative aspects and techniques. However, it should be understood that many variations and modifications can be made while remaining within the spirit and scope of the disclosure. Many alternatives, modifications and variations will be apparent to those skilled in the art in light of the foregoing description. Accordingly, this disclosure is intended to embrace all such alternatives, modifications, and variations that fall within the spirit and scope of the appended claims.

We claim:

1. An absorbent article for personal wear about a wearer's waist, the article comprising:
   a liquid permeable inner surface for facing the wearer;
   an outer surface for facing away from the wearer;
   an absorbent body disposed therebetween;
   a front waist region, a back waist region, and a crotch region extending longitudinally between and interconnecting the front and back waist regions;
   a pair of front side panels attached to the front waist region and a pair of back side panels attached to the back waist region, the front and back side panels being one of permanently attached and releasably attachable to define a wear configuration of the absorbent article having a waist opening and a pair of leg openings spaced from the waist opening, wherein the front and back side panels each extend from the waist opening to one of the leg openings, the article being configurable from the wear configuration to a disposal configuration in which the article is generally compacted for disposal; and
   a disposal tab having an attachment region with an attachment width and a tab region with a gripping width, the attachment region attached to one of the front or back side panels, the tab region being attachable to the article in at least the disposal configuration of the article, wherein the attachment width is substantially equal to the gripping width and wherein the tab region comprises a tab mechanical fastener and a gap region without a mechanical fastener and disposed between the tab mechanical fastener and the attachment region.

2. The article of claim 1, wherein the tab region has at least one substantially orthogonal corner distal from the attachment region.

3. The article of claim 1, wherein the tab is disposed adjacent the waist opening.

4. The article of claim 1, wherein each front side panel is releasably attached to one of the back side panels.

5. The article of claim 4, wherein one of the front and back side panels comprises an article mechanical fastener.

6. The article of claim 5, wherein at least a portion of the article mechanical fastener is disposed on one of the front side panels.

7. The article of claim 1, wherein the disposal tab is attached to one of the back side panels.

8. The article of claim 1, wherein the attachment of the front side panel to the back side panel is sufficient to maintain the article in a wear configuration during use of the article by the wearer.

9. The article of claim 1, wherein the tab region is releasably attached to a side panel when the article is in a wear configuration.

10. The article of claim 9, wherein such tab region releasable attachment is insufficient to maintain the article in a wear configuration during use of the article by the wearer.

11. The article of claim 1, wherein the disposal tab is folded back upon itself such that a portion of the tab mechanical fastener is in a face-to-face relationship with a portion of the attachment region, and such that portions of both the tab region and the attachment region are captured between a front side panel and a back side panel.

12. The article of claim 11, wherein the folded disposal tab does not extend beyond an edge of a front side panel or a back side panel.

13. The article of claim 1, further comprising an article fastening system for releasably attaching one of the front side panels to one of the back side panels, and a disposal fastening system separate from the article fastening system for selectively releasably attaching the tab region of the disposal tab to the article in each of the wear configuration and the disposal configuration of the article.

14. An absorbent article for personal wear about a wearer's waist, the article comprising:
 a liquid permeable inner surface for facing the wearer;
 an outer surface for facing away from the wearer;
 an absorbent body disposed therebetween;
 a front waist region, a back waist region, and a crotch region extending longitudinally between and interconnecting the front and back waist regions;
 a pair of front side panels attached to the front waist region and a pair of back side panels attached to the back waist region, the front and back side panels being releasably attachable to define a wear configuration of the absorbent article having a waist opening and a pair of leg openings spaced from the waist opening, wherein the front and back side panels each extend from the waist opening to one of the leg openings, the article being configurable from the wear configuration to a disposal configuration in which the article is generally compacted for disposal;
 an article fastening system for releasably attaching each front side panel to one of the back side panels, the article fastening system comprising an article mechanical fastener sufficient to maintain the article in a wear configuration during use of the article by the wearer;
 a disposal tab having an attachment region with an attachment width and a tab region with a gripping width, the attachment width being substantially equal to the gripping width, the attachment region attached to one of the front or back side panels, the tab region having at least one substantially orthogonal corner distal from the attachment region and a grip region, the grip region being disposed transversely outward of the attachment region and generally non-attachable to the article at least in the wear configuration of the article for use in gripping the tab region of the disposal tab; and
 a disposal fastening system at least in part separate from the article fastening system for selectively releasably attaching the tab region of the disposal tab to the article in each of the wear configuration and the disposal configuration of the article, the disposal fastening system comprising a disposal mechanical fastener insufficient to maintain the article in a wear configuration during use of the article by the wearer, the tab region includes a gap region without a mechanical fastener and disposed between the disposal mechanical fastener and the attachment region.

15. The article of claim 14, wherein the tab is disposed adjacent the waist opening.

16. The article of claim 14, wherein at least a portion of the article mechanical fastener is disposed on one of the front side panels, and wherein the disposal tab is attached to one of the back side panels.

17. An absorbent article for personal wear about a wearer's waist, the article comprising:
 a liquid permeable inner surface for facing the wearer;
 an outer surface for facing away from the wearer;
 an absorbent body disposed therebetween;
 a front waist region, a back waist region, and a crotch region extending longitudinally between and interconnecting the front and back waist regions;
 a pair of front side panels attached to the front waist region and a pair of back side panels attached to the back waist region, the front and back side panels being one of permanently attached and releasably attachable to define a wear configuration of the absorbent article having a waist opening and a pair of leg openings spaced from the waist opening, wherein the front and back side panels each extend from the waist opening to one of the leg openings, the article being configurable from the wear configuration to a disposal configuration in which the article is generally compacted for disposal; and
 a disposal tab having an attachment region with an attachment width and a tab region with a gripping width, the attachment region attached to one of the front or back side panels, the tab region being attachable to the article in at least the disposal configuration of the article, wherein the attachment width is substantially equal to the gripping width and wherein the tab region comprises a grip region without a mechanical fastener and distal from the side panel to which the disposal tab is attached.

* * * * *